United States Patent [19]

Chavkin et al.

[11] Patent Number: 4,988,679

[45] Date of Patent: Jan. 29, 1991

[54] LIQUID SUSTAINED RELEASE COMPOSITION

[76] Inventors: Leonard Chavkin, R.R. 1, P.O. Box 90, Bloomsbury, N.J. 08804; Leonard Mackles, 311 E. 23rd St., New York, N.Y. 10010

[21] Appl. No.: 367,851

[22] Filed: Jun. 19, 1989

Related U.S. Application Data

[63] Continuation-in-part of Ser. No. 293,194, Jan. 3, 1989.

[51] Int. Cl.$^5$ .................. A61K 31/715; A61K 47/00; A61K 31/61
[52] U.S. Cl. ........................................ 514/53; 514/54; 514/197; 514/263; 514/264; 514/289; 514/630; 514/574; 514/769; 514/770; 514/779; 514/786; 514/163
[58] Field of Search ............... 514/769, 770, 779, 786, 514/197, 289, 263, 264, 630, 574, 53, 54, 163

[56] References Cited

U.S. PATENT DOCUMENTS

| | | | |
|---|---|---|---|
| 3,984,571 | 10/1976 | Chen | 514/779 |
| 4,576,645 | 3/1986 | Ravel et al. | 514/779 |
| 4,639,367 | 1/1987 | Mackles | 424/45 |
| 4,747,881 | 5/1988 | Shaw | 514/779 |
| 4,843,098 | 6/1989 | Shaw et al. | 514/779 |
| 4,889,709 | 12/1989 | Mackles | 514/45 |

*Primary Examiner*—Frederick E. Waddell
*Attorney, Agent, or Firm*—Omri M. Behr

[57] ABSTRACT

There is provided an orally ingestible liquid composition for suspending therein an orally administrable pharmaceutically active composition releasable over an extended period of time comprises triglyceride of a medium chain length alkanoic acid or distilled acetylated monoglycerides, a liquid, high HLB polyglyceryl ester, and colloidal silicon dioxide together with a material soluble or dispersible therein and capable of being insolubilized by a pharmaceutically acceptable polyvalent cation and a solid pharmaceutically acceptable salt containing the cation required therefore. Sustained release compositions based thereon containing pharmaceutically active agents are also disclosed.

19 Claims, No Drawings

LIQUID SUSTAINED RELEASE COMPOSITION

RELATED APPLICATIONS

This application is a continuation in part of our copending application Ser. No. 07/293,194 filed Jan. 3, 1989, whose disclosure is incorporated herein by reference.

FIELD OF THE INVENTION

Orally ingestible compositions for the sustained release of pharmaceutically active substances.

BACKGROUND OF THE INVENTION

Conventional techniques for achieving sustained or delayed release of medicaments for oral ingestion involve the pre-treatment of the drug with a material to make it less soluble in the fluids of the stomach and the intestinal tract. Water-insoluble film forming polymers are widely used for this purpose as are waxes and fats that require digestion by the bile fluids to release entrapped medication.

Materials are also commonly employed which erode gradually or develop porosity to release entrapped medicaments. These can involve similar polymers or waxes that form the structures or gels through which the aqueous digestive fluids can travel to extract the medication and make it available for absorption.

In general, these techniques for achieving delayed drug availability require rather complex methodologies for coating the particles of drug or for preparing the dosage form of the drug. This complexity introduces a dimension of variability which makes it necessary to carefully monitor the rate of drug release of each batch of product in-vitro by measuring drug dissolution against some standard in order to assure the reproducibility of drug delivery form each batch of finished product.

During experimentation on the orally ingestible compositions disclosed in the parent application hereof, it was noted that when the compositions which contained soluble alginates and antacids in the form of polyvalent cation salts were exposed to hydrochloric acid of stomach acid strength, the compositions formed a gummy glutinous adhesive mass out of which the major antacid portion leached slowly, rather than rapidly as initially expected. Further investigations led to the formulation of the compositions disclosed and claimed herein.

SUMMARY

There is provided an orally ingestible liquid composition for suspending therein at least one orally administrable pharmaceutically active composition releasable over an extended period of time comprising a triglyceride of a medium chain length alkanoic acid or distilled acetylated monoglycerides, a liquid, high HLB polyglyceryl ester and colloidal silicon dioxide together with a material soluble or dispersible therein and capable of being insolubilized by a pharmaceutically acceptable polyvalent cation and a solid pharmaceutically acceptable salt containing the cation required therefore.

The actual adminstrable composition further comprises at least one pharmaceutically active composition.

DESCRIPTION OF THE PREFERRED EMBODIMENTS

There is provided an orally ingestible suitably anhydrous liquid composition for suspending therein at least one orally administrable pharmaceutically active composition releasable over an extended period of time comprising about 30 to about 90 parts by weight of at least one triglyceride of a medium chain length alkanoic acid wherein the said acid has between 8 and 10 carbon atoms in the chain, distilled acetylated monoglycerides, about 2 to about 10 parts by weight of a hydrophilic surfactant, suitably a liquid, high HLB polyglyceryl ester, and about 1 to about 6 parts by weight of colloidal silicon dioxide, as well as about 0.5 to about 5.0 parts by weight of a material soluble or dispersible therein and capable of being insolubilized by a pharmaceutically acceptable polyvalent cation and about 5 to about 20 parts by weight of a solid pharmaceutically acceptable salt containing the cation required therefore. Optionally there are also utilized flavorings and sweetness to 0.2 to 1 part by weight and sugar at between about 1.0 and 5.0 parts by weight to a total of 100 parts by weight.

The actual administrable composition further comprises about 0.1 to about 40 parts by weight of the pharmaceutically active composition to a total of 100 parts by weight.

Preferably, the alkanoic acid is caprylic or capric acid, the surfactant ester is liquid at least 20° C. and the HLB is at least 8.0 and is suitably at least one member of the group consisting of hexaglyceryl monooleate, octaglyceryl monooleate and hexaglyceryl dioleate. It is desirable that silicon dioxide is hydrophilic fumed silicon dioxide.

As the solubilizable insoluble material there may be used lecithin and/or the water soluble, pharmaceutically acceptable slats of alginic acid suitably those of sodium, potassium and magnesium. Most suitably there is employed lecithin and an alginate.

As the pharmaceutically active agent there may be selected any orally administrable agent, suitably a member of the group consisting of inorganic gastric acid neutralizing agents, gums used as gastric ulcer relief agents, mucosal bioadhesives and anti gastric ulcer agents.

In addition the compositions hereof may be utilized to provide sustained action to a variety of pharmacologically active medicinal agents. Such agents include antibiotics, such as amoxicillin, antitussives such as dextromethorphan hydrobromide (both per se and in combination with decongestants and antihistamines), antiasthmatics such as theophylline and analgesics such as aspirin or acetaminophen.

The recitation of these specific agents is intended merely as illustration and not as limitation.

Suitably, as neutralizing agents there may be utilized a basic salt of aluminium, magnesium, bismuth and calcium or a hydroxide or a carbonate thereof. These neutralizing agents, when present, also sere as the source of desolubilizing cation.

As gums there may be used carrageenan, alginic acid and the pharmaceutically acceptable alkali metal salts thereof. There may also be employed bioadhesives such as polycarbophil and anti ulcer agents such as sucralfate.

When the composition described above encounters the hydrochloric acid of the stomach, the divalent calcium ions released form the calcium carbonate or the polyvalent cations released from the other basic salts, will react to insolubilize the lecithin dissolved in the oil or the soluble alginate dissolved in the stomach contents.

Thus the products of the reaction of the lecithin and/or alginate with polyvalent cations, e.g., calcium, magnesium and the like, form a mucoadhesive sticky film that envelopes the suspended active medicament and holds it to the lining of the stomach to provide for its gradual release through dissolution.

Since the rate of release of active medicament is a function of the composition of the vehicle and does not depend upon some complex coating technology, batch variability will be very low. Once the desired release rate is achieved, the formulation can be fixed and quality can be assured by only occasional in-vitro assays.

The factors that affect the rate or release of the medicament from the matrix formed by the compositions of the invention are:
1. The concentration and solubility of the medicament. Large doses of insoluble substances will be released most slowly.
2. The concentration of waxy and/or polymeric material used.
3. The concentration of hydrophilic surfactant, e.g., Hexaglyceryl Monooleate used. The higher the concentration, the more rapid the rate of active ingredient release.

The unique sustaining mucoadhesive action of the composition can be observed in-vitro by dispersion in water followed by gradual addition of hydrochloric acid to mimic the conditions encountered in the stomach. Initially, dispersion in water is rapid and uniform but when acid is added, a coagulum is slowly formed that sticks to the walls of the container leaving a clear supernatant liquid.

It has been shown that this effect enables the formulated product to deliver a suspended medicament in sufficient quantity to achieve an initial desired effect and that the coagulum slowly releases additional drug for the maintenance of therapeutic action.

The results in Table 1 show the influence of the three release rate regulating agents upon the initial bio-availability of the antacids in Formulas A and B. It is clear that lecithin and potassium alginate reduce the initial availability of the antacids and that the surfactant, hexaglyceryl monooleate increased the rate of release of these drugs.

TABLE 1

Antacid Effectiveness expressed in terms of Acid Neutralizing Capacity (ANC) as determined by method in United States Pharmacopeia XXI, p. 1264
ANC (for 10 ml. dose)

| EX | A | B |
|---|---|---|
| 1. Antacid | 102 | 97 |
| 2. Antacid plus potassium alginate 2% Lecithin 1% Hexaglyceryl monooleate at 4% | 23 | 39 |
| 3. Antacid in (2) + 4% additional Hexaglyceryl monooleate | 44 | 50 |
| 4. Antacid plus potassium alginate 1% Lecithin 2% Hexaglyceryl monooleate at 4% | | 36 |
| 5. Antacid in (4) + 4% additional Hexaglyceryl monooleate | | 55 |
| 6. Antacid plus lecithin 3% Hexaglyceryl monooleate at 4% | | 16 |

The foregoing results show that if the USP acid consuming power test is applied to the product without the potassium alginate and lecithin, a value of 97 or 102 milliequivalents per 10 ml. does is obtained, which is close to theoretical.

If the same test is used on the complete product, the result is 55 milliequivalents showing that about 55% of the antacid is available for immediate activity.

If a modified version of the USP test is continued for a time period double that of the normal test duration, an addition 27 milliequivalents are found to become available. And, if the test is tripled, a total of 86 milliequivalents or about 91% of the total antacid contained in the product is made available.

It is also understood that the mechanism that is responsible for the sustained release is not specific to the antacid but would be effective for any medication and could be applied to similar formulations of other drugs.

EXAMPLES

Example 1

Antacid formulations without insolubilizing agents

| Antacid A | % by Wt. | Antacid B | % by wt |
|---|---|---|---|
| Aluminum hydroxide dried gel USP | 15.0 | Aluminum Hydroxide dried gel USP | 10.00 |
| Magnesium hydroxide USP fine powder | 15.0 | Magnesium hydroxide USP fine powder | 10.00 |
| | | Calcium carbonate, USP fine powder | 10.00 |
| Hexaglyceryl Monooleate | 8.0 | Hexaglyceryl monooleate | 8.00 |
| Colloidal Silicon dioxide NF | 2.0 | Colloidal silicon dioxide NF | 1.25 |
| Medium Chain triglycerides | 49.7 | Medium chain triglycerides | 50.45 |
| Sugar 12x NF | 10.0 | Sugar 12X NF | 10.00 |
| Flavors and sweetners | 0.3 | Flavor and sweetners | 0.30 |
| | 100.00% | | 100.00% |

Example 2

Formulation of Example 1 plus

| | A | B |
|---|---|---|
| Potassium alginate | 2% | 2% |
| Lecithin | 1% | 1% |
| Hexaglyceryl monooleate | (−4%) | (−4%) |

Example 3

Formulation of Example 1 plus

| | A | B |
|---|---|---|
| Potassium alginate | 2% | 2% |
| Lecithin | 1% | 1% |

Example 4

Formulation of Example 1 plus

| | B |
|---|---|
| Potassium alginate | 1% |

-continued

| | B |
|---|---|
| Lecithin | 2% |
| Hexaglyceryl monooleate | (−4%) |

Example 5

Formulation of Example 1 plus

| | B |
|---|---|
| Potassium alginate | 1% |
| Lecithin | 2% |

Example 6

Formulation of Example 1 plus

| | B |
|---|---|
| Lecithin | 3% |
| Hexaglyceryl (−4%) monooleate | (−4%) |

Example 7

General Formula for Sustained Action Vehicle (Composition)

| | % by weight |
|---|---|
| 1. Sugar, flavor, color, sweetner | 5–10 |
| 2. MCT or AMG | 40–85 |
| 3. Lecithin and/or soluble Alginate | 1.0–5.0 |
| 4. Hydrophilic Surfactant | 2.0–10.0 |
| 5. Colloidal Silicon Dioxide | 1.0–5.0 |
| 6. Insolubilizing Cation-salt (e.g. Calcium Carbonate) | 5.0–20.0 |
| 7. Medicament-suspended | 0.1–40.0 |
| | 100% |

Example 8

Ratio of Lecithin to Soluble Alginate

| Slower release (%) | Faster Release (%) |
|---|---|
| 25 | 75 |
| 50 | 50 |
| 75 | 25 |

Example 9

Formula for Sustained Action Aspirin

| Active dose: 1 g. Aspirin/5 ml suspension | % W/V |
|---|---|
| 1. Sugar 12X NF | 10% |
| 2. Acetylated Monoglycerides enough to make | 100 V % |
| 3. Lecithin | 3.0 |
| 4. Potassium Alginate | 2.0 |
| 5. Hexaglyceryl dioleate | 6.0 |
| 6. Colloidal Silicon Dioxide NF | 5.0 |
| 7. Calcium Carbonate | 6.0 |
| 8. Saccharin, acid | 0.2 |
| 9. Flavor | 0.5 |
| 10. Aspirin USP powder, 100 mesh | 20.0 |
| | 100% |

Adult Dose: 1–2 teaspoonfuls every 12 hours for arthritis.

Example 10

Formula for Sustained Action Amoxicillin

| Active dose: 250 mg. Amoxicillin/5 ml suspension | % W/V |
|---|---|
| 1. Sugar 12X NF | 10% |
| 2. Acetylated Monoglycerides enough to make | 100 V % |
| 3. Lecithin | 1.0 |
| 4. Potassium Alginate | 3.0 |
| 5. Hexaglyceryl monooleate | 4.0 |
| 6. Colloidal Silicon Dioxide NF | 2.0 |
| 7. Calcium Carbonate | 5.0 |
| 8. Saccharin, acid | 0.1 |
| 9. Flavor | 0.5 |
| 10. Amoxicillin Trihydrate | 5.0 |
| | 100% |

Children's Dose: ½–2 teaspoonfuls every 12 hours.

Example 11

Formula for Sustained Action Theophylline

| Active dose: 200 mg. Theophilline/5 ml suspension | % W/V |
|---|---|
| 1. Sugar 12X NF | 10% |
| 2. Acetylated Monoglycerides enough to make | 100 V % |
| 3. Lecithin | 2.0 |
| 4. Sodium Alginate | 2.0 |
| 5. Hexaglyceryl dioleate | 8.0 |
| 6. Colloidal Silicon Dioxide NF | 3.0 |
| 7. Magnesium Carbonate | 5.0 |
| 8. Saccharin, acid | 0.2 |
| 9. Flavor | 0.5 |
| 10. Theophylline, anhydrous fine powder | 20.0 |
| | 100% |

Children's Dose: 1–2 teaspoonfuls every 12 hours.

Example 12

Formula for Sustained Action Antitussive

Active dose: 30 Mg. Dextromethorphan HBr/5 ml % W/V suspension

| Active dose: 30 Mg. Dextromethorphan HBr/5 ml suspension | % W/V |
|---|---|
| 1. Sugar 12X NF | 10% |
| 2. Acetylated Monoglycerides enough to make | 100 V % |
| 3. Lecithin | 1.0 |
| 4. Sodium Alginate | 3.0 |
| 5. Octaglyceryl monooleate | 6.0 |
| 6. Colloidal Silicon Dioxide NF | 2.0 |
| 7. Magnesium Carbonate | 5.0 |
| 8. Saccharin, acid | 0.2 |
| 9. Flavor | 0.5 |
| 10. Dextromethorphan HBr 10% Adsorbate | 6.0 |
| | 100% |

Children's Dose: ½–2 teaspoonfuls every 12 hours.

We claim:

1. An orally ingestible liquid composition for suspending therein at least one orally administrable pharmaceutically active composition, said composition being releasable over an extended time period comprising:

(i)

(a) about 30 to about 90 parts by weight of a member selected from the group consisting of at least one triglyceride of a medium chain length alkanoic acid wherein the said acid has between 8 and 10 carbon atoms in the chain and distilled acetylated monoglycerides,
  (b) about 2 to about 10 parts by weight of a liquid, polyglyceryl ester of HLB of at least 8,
  (c) about 1 to about 6 parts by weight of colloidal silicon dioxide,
 (ii) about 0.5 to about 5.0 parts by weight of a material soluble or dispersible in (i) selected from the group consisting of lecithin and the water soluble pharmaceutically acceptable salts of alginic acid and capable of being insolubilized by a pharmaceutically acceptable polyvalent cation,
 (iii) about 5 to about 20 parts by weight of a solid pharmaceutically acceptable salt containing the cation required in (ii) to a total of 100 parts by weight.

2. A composition of claim 1 wherein the alginic acid salts are those of sodium potassium and magnesium.

3. A composition of claim 1 wherein the material of (ii) comprises lecithin and an alginate.

4. A composition of claim 1 wherein the alkanoic acid of (a) is caprylic or capric acid.

5. A composition of claim 1 wherein the ester is liquid at least 20° C.

6. A composition of claim 5 wherein the ester is selected from at least one member of the group consisting of hexaglyceryl monooleate, octaglyceryl monooleate and hexaglyceryl dioleate.

7. A composition of claim 1 wherein the silicon dioxide is hydrophilic fumed silicon dioxide.

8. An orally ingestible liquid composition having suspended therein at least one orally administrable pharmaceutically active composition, said composition being releasable over an extended time period comprising:
  (a) about 30 to about 90 parts by weight of a member selected from the group consisting of at least one triglyceride of a medium chain length alkanoic acid wherein the said acid has between 8 and 10 carbon atoms in the chain and distilled acetylated monoglycerides.
  (b) about 2 to about 10 parts by weight of a liquid, polyglyceryl ester of HLB of at least 8,
  (c) about 1 to about 6 parts by weight of colloidal silicon dioxide and
 (ii) about 0.5 to about 5.0 parts by weight of a material soluble or dispersible in (i) and capable of being insolubilized by a pharmaceutically acceptable polyvalent cation selected from the group consisting of lecithin and the water soluble pharmaceutically acceptable salts of alginic acid,
 (iii) about 5 to about 20 parts by weight of a solid pharmaceutically acceptable salt containing the cation required in (ii) and
 (iv) about 0.1 to about 40 parts by weight, of a total composition of 100 parts by weight of said at least one pharmaceutically active composition, to a total of 100 by weight.

9. A composition of claim 8 wherein the alginic acid salts are those of sodium potassium and magnesium.

10. A composition of claim 8 wherein the material of (ii) comprises lecithin and an alginate.

11. A composition of claim 8 wherein the alkanoic acid of (a) is caprylic or capric acid.

12. A composition of claim 8 wherein the ester is liquid at least 20° C.

13. A composition of claim 12 wherein the ester is selected from at least one member of the group consisting of hexaglyceryl monooleate, octaglyceryl monooleate and hexaglyceryl dioleate.

14. A composition of claim 8 wherein the silicon dioxide is hydrophilic fumed silicon dioxide.

15. A composition of claim 8 wherein at least one pharmaceutically active agent is selected from the group consisting of inorganic gastric acid neutralizing agents, gums used as gastric ulcer relief agents, mucosal bioadhesives and anti gastric ulcer agents, antibiotics, antitussives per se and in combination with decongestants and antihistamines, antiasthmatics and analgesics.

16. A composition of claim 15 wherein at least one pharmaceutically active agent is selected from the group consisting of inorganic gastric acid neutralizing agents, gums uses as gastric ulcer relief agents, mucosal bioadhesives and anti gastric ulcer agents.

17. A composition of claim 15 wherein at least one pharmaceutically active agent is selected from the group consisting of antibiotics, antitussives per se and in combination with decongestants and antihistamines, antiasthmatics and analgesics.

18. A composition of claim 17 wherein at least one pharmaceutically active agent is selected from the group consisting of amoxicillin, dextromethorphan hydrobromide, theophylline and aspirin and acetaminophen.

19. A composition of claim 16 wherein at least one pharmaceutically active agent is selected from the group consisting of polycarbophil and sucralfate.

* * * * *